United States Patent [19]
Bischoff et al.

[11] Patent Number: 6,066,166
[45] Date of Patent: May 23, 2000

[54] MEDICAL ELECTRICAL LEAD

[75] Inventors: Thomas C. Bischoff, Minneapolis; Mark T. Marshall, Forest Lake; James J. Snyder, Blaine; Sandra F. Viktora, Coon Rapids, all of Minn.

[73] Assignee: Medtronic, Inc., Minneapolis, Minn.

[21] Appl. No.: 09/143,504

[22] Filed: Aug. 28, 1998

[51] Int. Cl.$^7$ .................................................. A61N 1/05
[52] U.S. Cl. .............................................................. 607/122
[58] Field of Search ...................................... 607/122, 123, 607/119, 116

[56] References Cited

U.S. PATENT DOCUMENTS

| | | |
|---|---|---|
| 4,355,646 | 10/1982 | Kallok et al. . |
| 4,603,705 | 8/1986 | Speicher et al. . |
| 4,614,192 | 9/1986 | Imran et al. . |
| 5,476,501 | 12/1995 | Stewart et al. . |
| 5,584,873 | 12/1996 | Shoberg et al. . |
| 5,760,341 | 6/1998 | Laske et al. . |

*Primary Examiner*—Scott M. Getzow
*Attorney, Agent, or Firm*—Reed A. Duthler; Harold R. Patton

[57] ABSTRACT

An implantable cardioversion/defibrillation lead having an elongated insulative lead body carrying a tip electrode located at its distal end and a cardioversion/defibrillation electrode located on the lead body, proximal to the tip electrode. An elongated conductor coupled to the tip electrode extends proximally within the lead body. At the proximal end of the lead body is a first connector assembly carrying a first connector and a second connector assembly carrying a second connector. An elongated, stranded or cabled conductor is coupled to the cardioversion/defibrillation electrode and to the second connector and extends uninterrupted therebetween. A cylindrical transition member is coupled to the first connector by means of a coiled conductor. A press-fit sleeve having a longitudinal lumen extending therethrough compresses the stranded or conductor between the press-fit sleeve and the transition member to provide electrical interconnection between the stranded or cabled conductor and the transition member.

7 Claims, 3 Drawing Sheets

MEDICAL ELECTRICAL LEAD

BACKGROUND OF THE INVENTION

The present invention relates generally to implantable medical leads and more specifically to pacemaker and defibrillation leads employing stranded conductors.

Traditionally, implantable cardiac pacing and defibrillation leads have employed monofilar or multifilar coiled conductors, as illustrated in U.S. Pat. No. 4,355,646 issued to Kallok et al. More recently, cabled or stranded conductors have gained wider acceptance, for example, as disclosed in U.S. Pat. No. 5,584,873 issued to Shoberg et al. and incorporated herein by reference in its entirety and U.S. Pat. No. 5,760,341 issued to Laske et al., also incorporated herein by reference in its entirety. In conjunction with the use of stranded conductors, new mechanisms for interconnecting the conductors to other electrically conductive lead components have had to be developed. One such mechanism for coupling stranded conductors to electrical components in a lead is a press-fit sleeve, as disclosed in U.S. patent application Ser. No. 08/439,332 for a "Medical Lead With Stranded Conductors", filed May 11, 1995 by Swoyer et al, also incorporated herein by reference in its entirety.

In the particular context of defibrillation leads, use of the electrodes on the leads to sense electrical signals in a bipolar fashion has typically been accomplished by one of two ways. The first mechanism for accomplishing bipolar sensing is to simply provide a tip electrode and a ring electrode, as commonly used in bipolar cardiac pacing leads, for example as illustrated in U.S. Pat. No. 4,614,192 issued to Imran et al. Alternatively, bipolar sensing can be provided by means of what has come to be known as an "integrated bipolar" system, wherein one of the defibrillation electrodes on the lead also serves as a sensing electrode, in conjunction with the distal or tip electrode on the lead. A lead employing an integrated bipolar electrode system is disclosed in U.S. Pat. No. 4,603,705 issued to Speicher et al. In such a lead, it is necessary to couple the defibrillation electrode which also serves as the sensing electrode to separate electrical connectors, so that it may be coupled to the input terminal of the sense amplifier on an associated implantable cardioverter/defibrillator and to the cardioversion/defibrillation output terminal.

While the lead illustrated in the Speicher patent employs separate connector pins for each connection to the pulse generator, it has become more common to connect sensing electrodes using a bipolar in-line connector conforming to the IS-1 connector standard, typically employed on leads intended for use with implantable pacemakers, as disclosed in U.S. Pat. No. 5,476,501 issued to Stewart et al., incorporated herein by reference in its entirety. In the context of a lead which employs an advanceable fixation helix located at its distal end, it is conventional to employ a coiled conductor, rotatable within the lead body and coupled to a rotatable connector pin extending from the proximal end of the connector assembly as the mechanism for rotating the fixation helix, as also disclosed in U.S. Pat. No. 5,476,501 issued to Stewart et al.

SUMMARY OF THE INVENTION

The present invention is directed toward a cardioversion/defibrillation lead which employs integrated bipolar sensing between a tip or distal electrode and an adjacent cardioversion electrode. The lead preferably employs an IS-1 type in-line bipolar connector assembly and in a preferred embodiment of the invention, the lead is provided with an electrode taking the form of a rotatable fixation helix, advanced and retracted by means of a rotatable, coiled conductor extending to a rotatable connector pin on the proximal end of the in-line connector assembly. The defibrillation electrode is coupled to a stranded or cabled conductor, which in turn is coupled both to a connector ring on the in-line connector assembly and to a connector pin on a separate connector assembly for connection to the output of the cardioverter/defibrillator. The present invention provides a simple, elegant and inexpensive mechanism for providing the required interconnection between the various conductors, electrodes and connectors described above.

In particular, the present invention provides for interconnection of the stranded conductor coupled to the defibrillation electrode to a coiled conductor coupled to an connector, preferably the connector ring on the in-line connector assembly. The invention provides a connection mechanism which allows the stranded conductor to continue uninterrupted to a connector on a separate connector assembly, intended to couple the cardioversion/defibrillation pulse generator. The connection is made by means of a press-fit sleeve in conjunction with a cylindrical transition flange. The transition flange is coupled at its proximal end to the coiled conductor and in a preferred embodiment is provided with external threading along its distal portion. The press-fit sleeve in a preferred embodiment is generally a cylindrical sleeve, located exterior to the distal, threaded portion of the transition flange, and compressing the stranded or cabled conductor against the outer surface of the transition sleeve, providing for mechanical and electrical interconnection of the coiled conductor and the stranded conductor.

The stranded conductor extends proximally from the press-fit sleeve to a connector located on a separate connector assembly and extends distally to the defibrillation electrode. In a preferred embodiment, the transition flange, stranded conductor and press-fit sleeve are assembled by passing the insulated stranded conductor through the press-fit sleeve and sliding the press-fit sleeve over the distal end of the transition flange, such that the threading on the exterior of the transition flange causes flow of insulation on the stranded conductor into the spaces between the threads on the transition flange, allowing for electrical interconnection without the necessity of stripping or removing insulation from the stranded conductor. Because the stranded conductor extends uninterrupted from the defibrillation electrode to the cardioversion/defibrillation pulse generator, a lead construction having a high tensile strength is provided. The transition flange is also provided with a longitudinal internal lumen, through which a coiled conductor coupled to the tip electrode may pass. This construction also allows for the use of a rotatable coiled conductor in the preferred embodiment in which the distal or tip electrode takes the form of a rotatable helix.

DETAILED DESCRIPTION OF THE PREFERRED EMBODIMENT OF THE INVENTION

Figure 1:
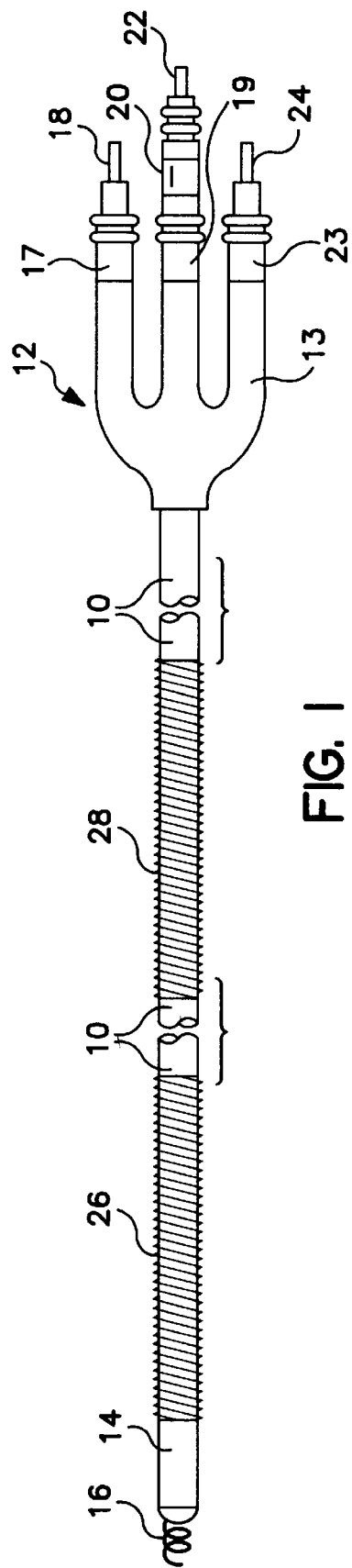
FIG. 1 is a plan view of a first embodiment of the invention.

FIG. 1 is a plan view of a lead incorporating a first embodiment of the invention. The lead is provided with an elongated insulative lead body 10 which may be fabricated of polyurethane or silicone rubber or other less rigid, elastic, relatively softer biocompatible plastic. The lead body carries at its distal end an insulative electrode head 14, which may also be fabricated of a relatively more rigid biocompatible plastic, such as a polyurethane and which carries an advanceable helical electrode 16. At its proximal end, the lead carries a trifurcated connector module 12 comprising a molded trifurcation sleeve 13, from which three insulative tubular sleeves 17, 19 and 23 extend. Sleeve 19 carries a first connector assembly which is an IS-1 compatible, in-line connector assembly provided with a connector ring 20 coupled to cardioversion/defibrillation electrode 26, and a connector pin 22 coupled to helical electrode 16. Sleeve 17 carries a second connector assembly provided with a connector pin 18, also coupled to cardioversion/defibrillation electrode 26 by means of a the mechanism discussed above. Sleeve 23 carries a third connector assembly provided with a connector pin 24, coupled to cardioversion/defibrillation electrode 28.

Figure 2:
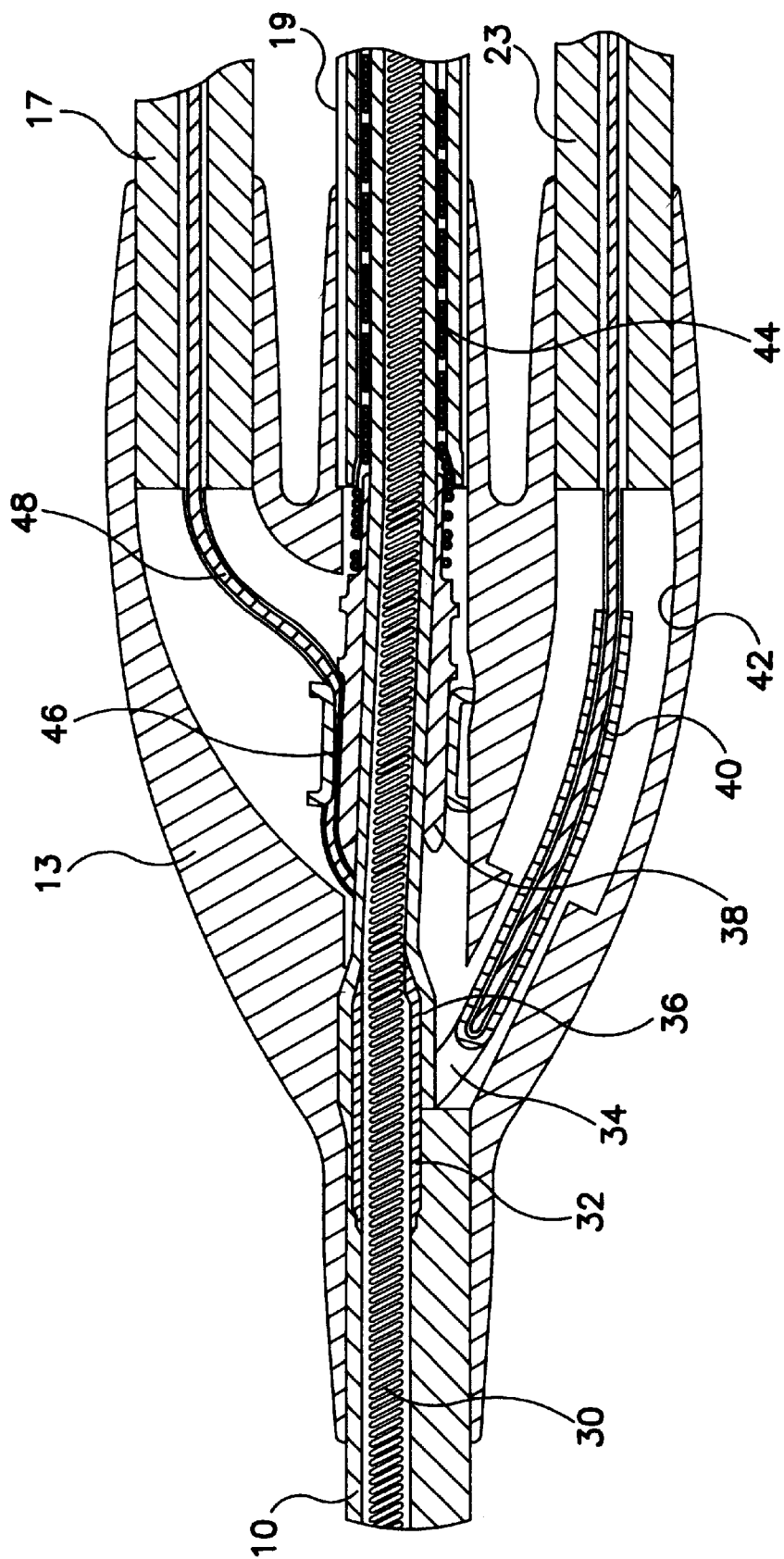
FIG. 2 is a sectional view through the proximal portion of the lead illustrated in FIG. 1 in the vicinity of the trifurcation sleeve.

FIG. 2 is a sectional view of the lead through FIG. 1 in the vicinity of the trifurcation sleeve 13, which may be molded of silicone rubber, polyurethane or other biocompatible plastic. The proximal portion of the lead body 10 terminates within the distal portion of the trifurcation sleeve 13 and is an extruded multilumen tube of silicone rubber or other biocompatible plastic, including a first lumen enclosing rotatable coiled conductor 30 and second and third lumens, not visible in this view, enclosing insulated stranded or cabled conductors 40 and 48. Conductor 48 is provided with an insulative coating, for example a thin layer of polytetrafouroethylene and is coupled to cardioversion/ defibrillation electrode 26 (FIG. 1) and to connector pin 18 (FIG. 1). Conductor 40 is coupled to cardioversion/ defibrillation electrode 28 (FIG. 1) and to connector pin 24 (FIG. 1). Coiled conductor 30 is coupled to the rotatable helical electrode 16 (FIG. 1) at the distal end of the lead and to rotatable pin 22 (FIG. 1) at the proximal end of the lead. Conductor 48 is also coupled to the connector ring 20 (FIG. 1) of the lead by means of press-fit sleeve 46 and transition flange 38, which in turn is coupled to connector ring 20 (FIG. 1) by means of coiled conductor 44. The interconnection of conductors 44 and 48, transition flange 37, and press-fit sleeve 46 is discussed in more detail below.

Coiled conductor 30 is surrounded by insulative sleeves 32 and 36, which may be fabricated of silicone rubber, polyurethane or other biocompatible plastic, as it extends from the proximal end of lead body 30. Stranded conductor 40 is provided with an insulative coating, for example a thin layer of polytetrafouroethylene and is further provided with a tubular insulative sleeve 34 extending proximally from the proximal end of lead body 10. The internal cavity 42 within trifurcation sleeve 13 is backfilled with silicone rubber after assembly. Extending proximally from the trifurcation sleeve 13 are tubular insulative sleeves 17, 19 and 23, which extend to the connector assemblies illustrated in FIG. 1.

Interconnection of insulated stranded or cabled conductor 48, press-fit sleeve 46 and transition flange 38 is accomplished by simply passing the insulated conductor 48 through the sleeve 46 and sliding the sleeve 46 over the distal end of the transition flange 38, causing flow of the insulation on conductor 48 into the spaces between the threading on transition flange 38 and compressing the stranded conductor between the transition flange 38 and the press-fit sleeve 46 to provide an electrical and mechanical interconnection. The coiled conductor 44 is simply welded to the proximal portion of the transition sleeve in a conventional manner to provide interconnection of the transition flange 38 with the connector ring 20 (FIG. 1) located on the in-line bipolar connector assembly.

Figure 3:
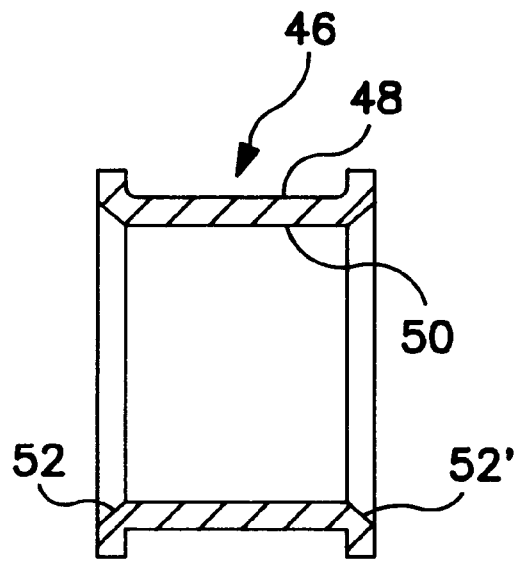
FIG. 3 is a sectional view through the press-fit sleeve illustrated in FIG. 2.

FIG. 3 is a sectional view through the press-fit sleeve 46. The sleeve is provided with an internal cylindrical lumen 50, and is provided with chamfers 52 on its proximal and distal ends. An external, circumferential groove 48 is provided which it engages with the assembly fixture employed to slide the press-fit sleeve 46 relative to the transition flange 38.

Figure 4:
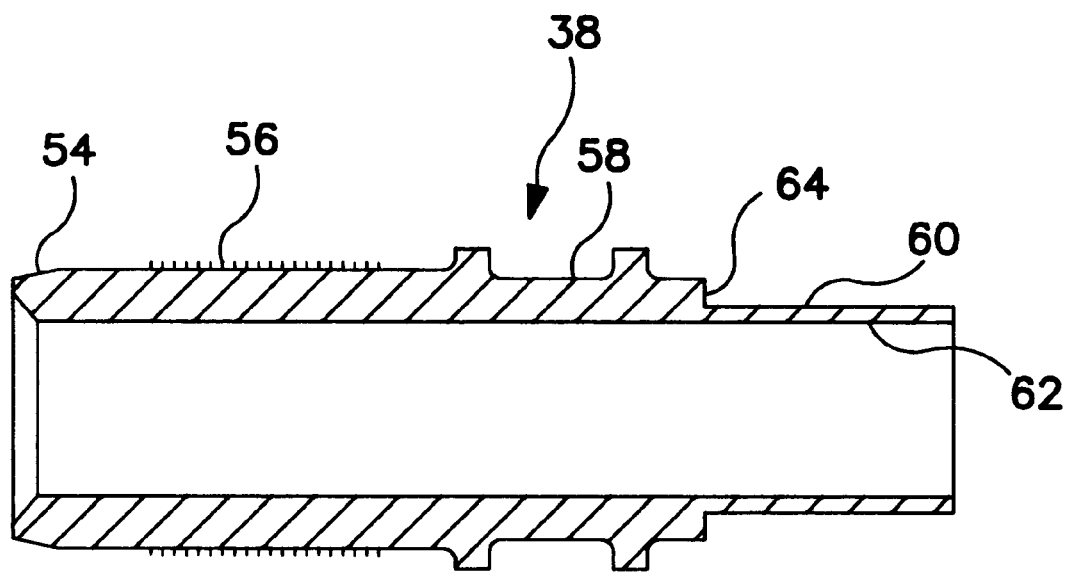
FIG. 4 is a sectional view through the transition flange illustrated in FIG. 2.

FIG. 4 is a sectional view through transition flange 3. Transition flange 38 is provided with an internal longitudinal lumen 62, allowing for passage of a coiled conductor therethrough. Flange 38 is provided with threading 56 on its distal portion and a chamfer 54, facilitating insertion of the flange 38 into press-fit sleeve 46. Flange 38 is provided with a reduced diameter proximal portion 60 over which the coiled conductor 44 (FIG. 2) is placed. The distal end of the coiled conductor 44 is welded against circumferential shoulder 64. Transition flange 38 is also provided with an external circumferential groove 58 which, like groove 48 (FIG. 3) is employed to engage the transition flange 38 with the assembly fixture employed to slide press-fit sleeve 46 over the distal portion of transition flange 38.

In conjunction with the above disclosure, we claim:

1. An implantable cardioversion/defibrillation lead comprising:
    an elongated insulative lead body having a proximal end and a distal end;
    a tip electrode located at the distal end of the elongated lead body;
    a cardioversion/defibrillation electrode located on the lead body, proximal to the tip electrode;
    an elongated conductor, coupled to the tip electrode;
    a first connector assembly located at the proximal end of the lead body, the first connector assembly carrying a first connector;
    a second connector assembly, located at the proximal end of the lead body, carrying a second connector;
    an elongated, stranded or cabled conductor coupled to the cardioversion/defibrillation electrode and to the second connector and extending uninterrupted therebetween;
    a cylindrical transition member;
    a press-fit sleeve having a longitudinal lumen extending therethrough, the stranded or cabled conductor extending through the lumen of the press-fit sleeve and compressed between the press-fit sleeve and the transition member to provide electrical interconnection between the stranded or cabled conductor and the transition member; and
    a coiled conductor, coupled to the transition member and to the first connector.

2. A lead according to claim 1 wherein the transition member is provided with a cylindrical lumen and wherein the electrical conductor extending from the tip electrode passes through the internal lumen of the transition member.

3. A lead according to claim 2 wherein the first connector assembly comprises an in-line connector assembly including said first connector and a third connector coupled to the electrical conductor coupled to the tip electrode.

4. A lead according to claim 3 wherein the electrical conductor coupled to the tip electrode takes the form of a coiled conductor.

5. A lead according to claim 4 wherein said tip electrode is a rotatable helical electrode and wherein the electrical conductor coupled thereto is also rotatable within the lead body.

6. A lead according to claim 1 or claim 2 or claim 3 or claim 4 or claim 5 wherein the stranded or cabled conductor is provided with an insulative coating along its length.

7. A lead according to claim 6 wherein the transition member is provided with external threading, which threading engages the cabled or stranded conductor.

* * * * *